US008091261B2

(12) United States Patent
Chadwick

(10) Patent No.: US 8,091,261 B2
(45) Date of Patent: Jan. 10, 2012

(54) BANDS FOR MAKING ADJUSTABLE LOOPS

(75) Inventor: Robert Chadwick, Haverhill, MA (US)

(73) Assignee: Endur ID Incorporated, Hampton, NH (US)

( * ) Notice: Subject to any disclaimer, the term of this patent is extended or adjusted under 35 U.S.C. 154(b) by 56 days.

(21) Appl. No.: 12/519,660

(22) PCT Filed: Dec. 20, 2007

(86) PCT No.: PCT/US2007/088333

§ 371 (c)(1), (2), (4) Date: Jun. 17, 2009

(87) PCT Pub. No.: WO2008/079952

PCT Pub. Date: Jul. 3, 2008

(65) Prior Publication Data

US 2010/0011643 A1 Jan. 21, 2010

Related U.S. Application Data

(60) Provisional application No. 60/870,947, filed on Dec. 20, 2006.

(51) Int. Cl.

*A44C 5/00* (2006.01)
*A61B 5/103* (2006.01)
*A61B 5/117* (2006.01)

(52) U.S. Cl. ................................ 40/633; 40/665; 40/304

(58) Field of Classification Search .................... 40/633, 40/665, 316, 661.09, 660, 638, 304; 283/75
See application file for complete search history.

(56) References Cited

U.S. PATENT DOCUMENTS

| | | | | |
|---|---|---|---|---|
| 1,146,754 | A * | 7/1915 | Evans | 292/315 |
| 4,914,843 | A * | 4/1990 | DeWoskin | 40/633 |
| 5,381,617 | A * | 1/1995 | Schwartztol et al. | 40/6 |
| 2004/0237366 | A1* | 12/2004 | Chadwick et al. | 40/633 |
| 2006/0254105 | A1* | 11/2006 | Chang | 40/633 |
| 2008/0028655 | A1* | 2/2008 | Riley | 40/633 |
| 2008/0236011 | A1* | 10/2008 | Bekker | 40/633 |

* cited by examiner

*Primary Examiner* — Joanne Silbermann
*Assistant Examiner* — Christopher E Veraa
(74) *Attorney, Agent, or Firm* — Onello & Mello, LLP

(57) ABSTRACT

Apparatus for forming a band into a persistent loop. The band incorporating the apparatus has a hole portion which contains a hole, a tongue portion which fits through the hole, and an adhesive attachment area on one or both of the hole and tongue portions. The band is made into a persistent loop by drawing the tongue portion through the hole and attaching the adhesive attachment area to the loop's outside surface. The size of the loop may be adjusted by varying the amount of the tongue portion which is drawn through the hole. A loop may be temporarily preformed by engaging a structure on the tongue portion with the hole. In embodiments in which the band is made of stiff material, the engaging structures may be the edges of the tongue portion and the edges of the hole. The disclosed embodiment of the apparatus is an identification band.

33 Claims, 5 Drawing Sheets

303

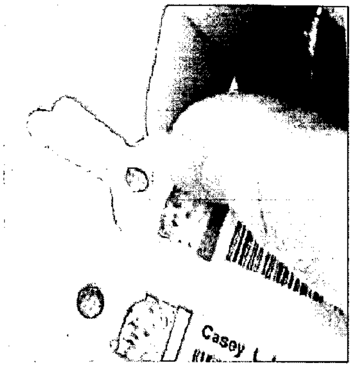

1) After the Infant Easy Band is printed, peel the band from the carrier sheet. Avoid touching the adhesive any more than necessary. Discard carrier sheet.

305

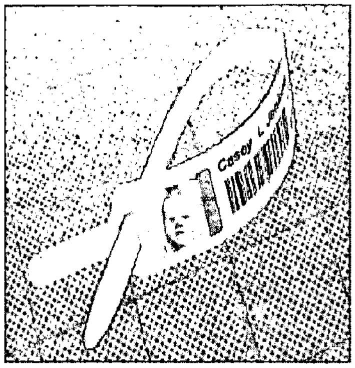

2) Prepare band for use by slipping tail of the band through the hole – set aside in this ready to use position until needed

305

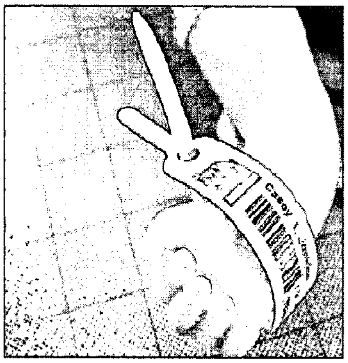

3) When ready, slip loose prepared band over wrist or ankle.

307

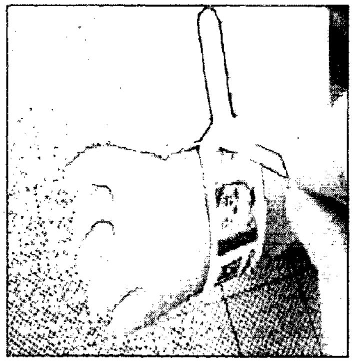

4) Grasp the tail and pull through hole until reaching the desired tightness. Be careful not to tighten too much, leave space under the band.

309

5) Secure band by pressing adhesive down and onto band.

311

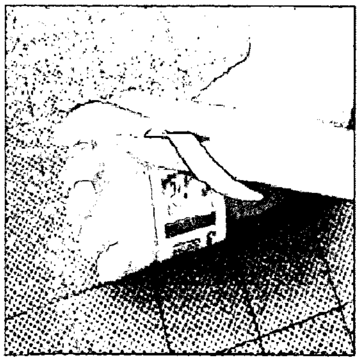

6) Trim off the excess tail and tuck end through hole to eliminate tail.

301

Fig. 3

BANDS FOR MAKING ADJUSTABLE LOOPS

CROSS-REFERENCE TO RELATED APPLICATIONS

The present patent application claims priority from U.S. Provisional Patent Application 60/870,947, Robert Chadwick, Wristband design and attachment method, filed Dec. 20, 2006. That application in its entirety is incorporated by reference for all purposes into the present patent application.

STATEMENT REGARDING FEDERALLY SPONSORED RESEARCH OR DEVELOPMENT

Not applicable.

REFERENCE TO A SEQUENCE LISTING

Not applicable.

BACKGROUND OF THE INVENTION

1. Field of the Invention

The invention concerns techniques for using bands made of sheet materials to make loops whose sizes are adjustable.

2. Description of Related Art

Bands made of sheet materials are often attached to items to identify them. One way of attaching the band to the item is to loop the band around part of the item. Examples of identification bands used in this fashion are the bands used to identify nursery stock, which are looped around the trunk or a branch of the nursery stock, and the wristbands used to identify patients in hospitals. Such bands need to be easily adjusted to make different-sized loops. In many cases, it is also important that the loop closely fits the object it is looped around and that there are no dangling ends. Examples of prior-art solutions to these problems may be found in U.S. published patent application 2004/0237366, Chadwick, et al., Identification bracelet, and U.S. Pat. No. 6, 641,048, Schintz, et al., Winged wristband. Finally, there are situations in which it is advantageous to make the loop in advance and then be able to adjust the loop to an exact fit after it has been placed on the object. It is an object of the techniques disclosed herein to provide bands made of sheet materials which are easily adjusted to closely fit an object, may be made up in advance, and which have no dangling ends.

BRIEF SUMMARY OF THE INVENTION

The foregoing object is attained by apparatus for forming a band into a persistent loop. The apparatus is made up of a hole portion of the band which contains a hole, a tongue portion of the band which fits through the hole, and adhesive attachment area on one or the other or both of the portions. To persistently form the band into a loop, one passes the tongue portion through the hole and attaches the adhesive attachment area to the loop's outer surface.

Other aspects of the apparatus may include the following:

- the tongue portion has a length which permits the size of the loop to be varied by varying the amount of the tongue portion which is passed through the hole.
- The tongue portion includes structures for mechanically engaging the hole, which permits the band to be temporarily formed into a loop prior to being persistently formed into the. The structures may be the edges of the tongue.

information areas which may be on the outside of the hole portion or on the outside of the tongue portion.

Another aspect of the techniques is business forms which include bands which implement the above apparatus. The business forms may include other entities that are linked to the bands by means of identification information which appears on both the bands and the other entities. The other entities may be labels or bands for persons who are associated with the wearer of a band which has the above apparatus. Yet another aspect of the invention is methods of forming bands which implement the above apparatus into loops.

Other objects and advantages will be apparent to those skilled in the arts to which the invention pertains upon perusal of the following Detailed Description and drawing, wherein:

BRIEF DESCRIPTION OF THE SEVERAL VIEWS OF THE DRAWINGS

FIG. 3 shows how the wristband of the preferred embodiment may be made up in advance and then adjusted to fit;

Figure 1:
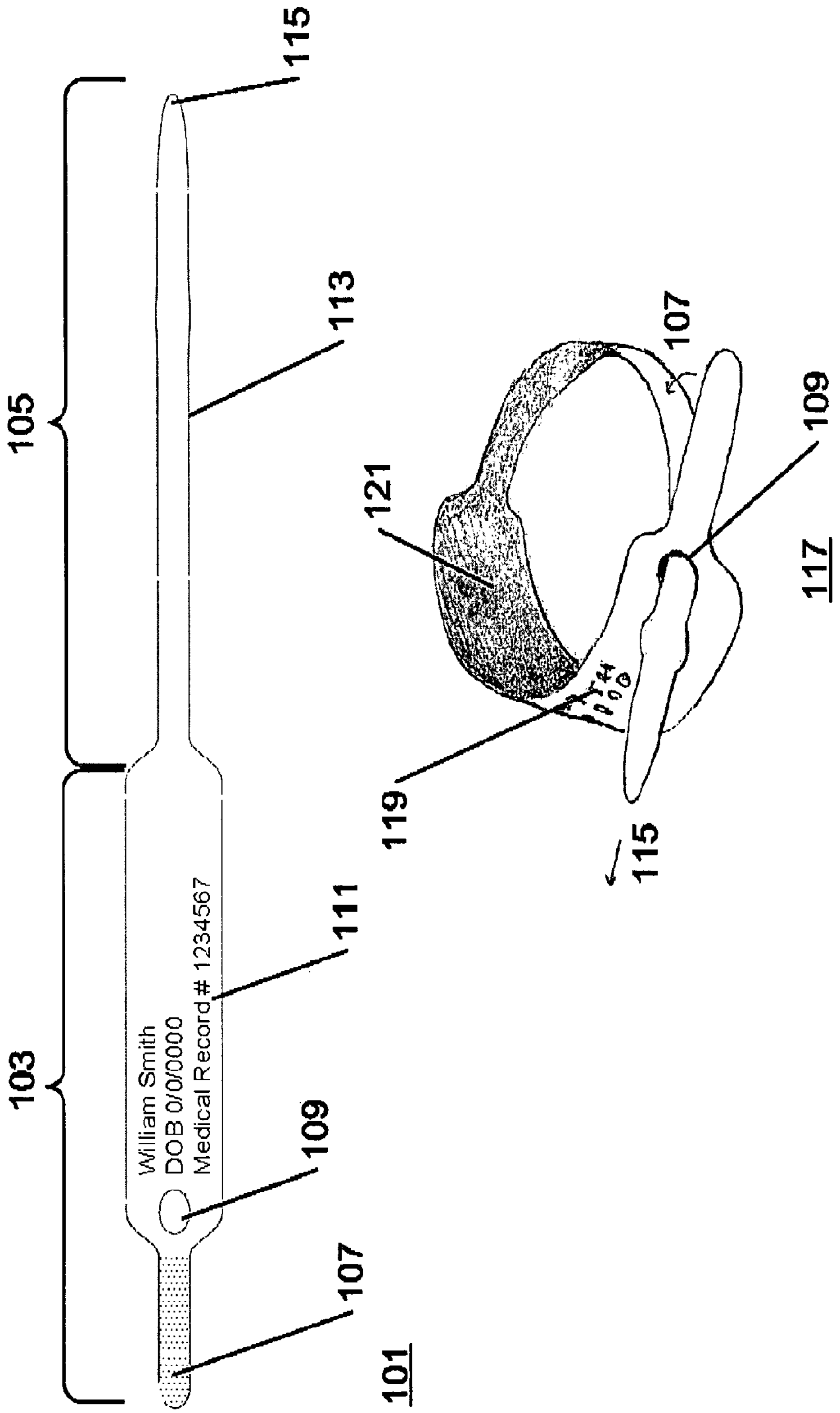
FIG. 1 shows a presently-preferred embodiment of a wristband which achieves the objects set forth above.

Reference numbers in the drawing have three or more digits: the two right-hand digits are reference numbers in the drawing indicated by the remaining digits. Thus, an item with the reference number 203 first appears as item 203 in FIG. 2.

DETAILED DESCRIPTION OF THE INVENTION

A wristband which can be made up in advance, is adjustable to fit, and has no hanging ends FIG. 1 shows a presently-preferred embodiment of a wristband which is made using the techniques disclosed herein. The presently-preferred embodiment of the wristband is designed for use in an institutional environment and is made of a sheet material which is waterproof and is resistant to solvents which are commonly employed in such environments. An example of such a sheet material is a cross laminated polyethylene film such as VALERON® produced by Valeron Strength Films of Houston Tex. The sheet material may further have a coating which renders water-based inks such as those used in ink-jet printers and marking pens water and solvent resistant. For details, see U.S. published patent application 2004/0237366. The sheet material may also be a material that is designed for use in Laser printers and is based upon polyesters or laminates of polyesters and polyolefins. An example of a film such as this would be "Tough paper" offered by Hewlett Packard Corporation or a custom-constructed material having the necessary properties. The sheet material employed for a particular embodiment of the bands will of course depend upon the use to which the bands are to be put.

FIG. 1 shows band 101 from which the preferred embodiment of the wristband is made. Band 101 has two major components: hole portion 103, which contains hole 109, and tongue portion 105. To make band 101 into a wristband, one inserts the end 115 of tongue portion 105 into hole 109. Tongue 105 is slightly wider than the diameter of hole 109. Consequently, tongue 105 must be bowed slightly to insert it into hole 109. The material of which wristband 101 is made has a stiffness which is approximately that of writing paper. Because tongue 105 is bowed slightly, the stiffness of the wristband's material urges the edges of tongue 105 against the edge of hole 109. The stiffness of the wristband's material also tends to force the loop made by passing tongue 105 through hole 109 to open, and the interaction between the edges of tongue 105 and hole 109 resists the tendency of the loop to open. Because of the interaction between the edges of the hole and the edges of tongue 105, band 101 may be premade into a temporary loop which has an adjustable size. The effect of the interaction between the edges of tongue 105 and hole 109 may be increased by including a slightly wider portion 113 in tongue 105. A wristband which has been premade from band 101 is shown at 117. The loop formed by the wristband has an outer surface 119 and an inner surface 121.

Hole portion 103 further includes information area 111, which contains information that has been written or printed on band 101, and adhesive attachment area 107. Information area 111 and the adhesive of adhesive attachment area 107 are on opposite sides of band 101; in the top view of band 101 of FIG. 1, the adhesive is on the other side of the band 101. When the wristband is finished, information area 111 will be on outer surface 119 of the loop. To give a wristband 117, premade or otherwise, its proper size, one places the wristband on the patient's extremity and pulls tongue 105 through hole 109 until the proper fit is obtained. Then one attaches adhesive attachment area 107 to outer surface 119 of the loop. The attachment of adhesive attachment area 107 to outer surface 119 gives the loop a persistent size. How persistent the size is will of course depend on the application for which the wristband is intended. Once the adhesive attachment area is attached, the portion of tongue 105 which protrudes beyond hole 109 may be cut off. If tongue 105 is cut off where it emerges from hole 109, the cut end will be retained by the edges of hole 109 and will not protrude above the outer surface of the wristband. In other versions, tongue 105 may include an adhesive attachment area at its end and the adhesive attachment area may be used to attach the end of tongue 106 to the outer surface of the loop.

Many variations of band 101 are possible. Fundamental to all of them are that the size of the band is adjusted by pulling tongue portion 105 through hole 109 and that the band is given its permanent size by attaching an adhesive attachment area to the outer surface of the loop. The adhesive attachment area may be on hole portion 103, as is the case with band 101, it may be on tongue portion 105, or there may be adhesive attachment areas on both hole portion 103 and tongue portion 105. The adhesive attachment areas may also include tabs which can be bent over and attached to the inner surface of the loop. The information area may be on hole portion 103, as in band 101, or on tongue 105.

Figure 2:
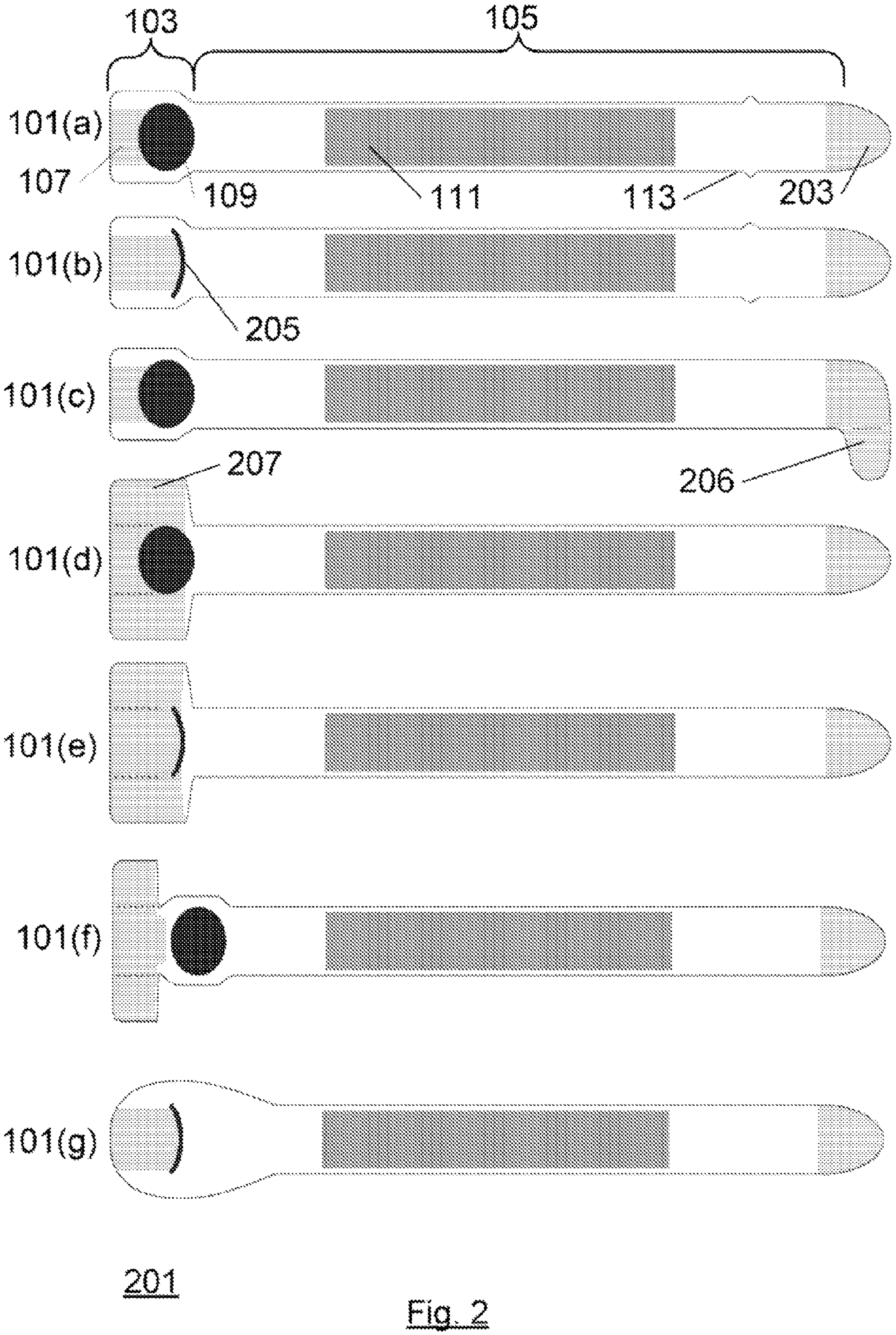
FIG. 2 shows other embodiments of such wristbands.

Exemplary Versions of Band 101: FIG 2

FIG. 2. shows versions 101(*a*) through 101(*g*) of a band 101, In all of these versions, there are two adhesive attachment areas: adhesive attachment area 107 on hole portion 103 and adhesive attachment area 203 at the end of tongue 105. In all of these versions, information area 111 is on tongue 105. As with band 101, information area 111 and the adhesive belonging to the adhesive attachment areas are on opposite sides of the band. Other variations include adhesive attachment areas with tabs as shown at 206 and 207 and different forms of hole 109, including a curved slit 205. An important consideration in the selection of a shape hole 109 is that the shape is one which does not tend to serve as a starting point for tears in the material from which the band is made. For cross laminated polyethylene and polyester films, the circle is such a shape.

An Exemplary Use of Band 101: FIG. 3

A use of band 101 which illustrates the value of being able to premake the loop is shown in FIG. 3. FIG. 3 is used to train nurses in the use of band 101 with newborn babies. To prevent mistakes in identifying the babies, the newborn must receive its identification wristband immediately after birth, before the newborn has been washed. At this point, the newborn is slippery and hard to handle. The figure shows the procedure 301 for placing the identification wristband on the baby. First, the band is printed (303). Then it is premade by placing tongue 105 through hole 109 and set aside (305). When the baby is born, the premade wristband is placed over the baby's wrist or ankle (305). Then the tongue is grasped and pulled to tighten the wristband to its permanent size (307). Next, adhesive attachment area 107 is attached to the band (309). Finally, tongue 105 is trimmed off at hole 109 (311).

Figure 4:
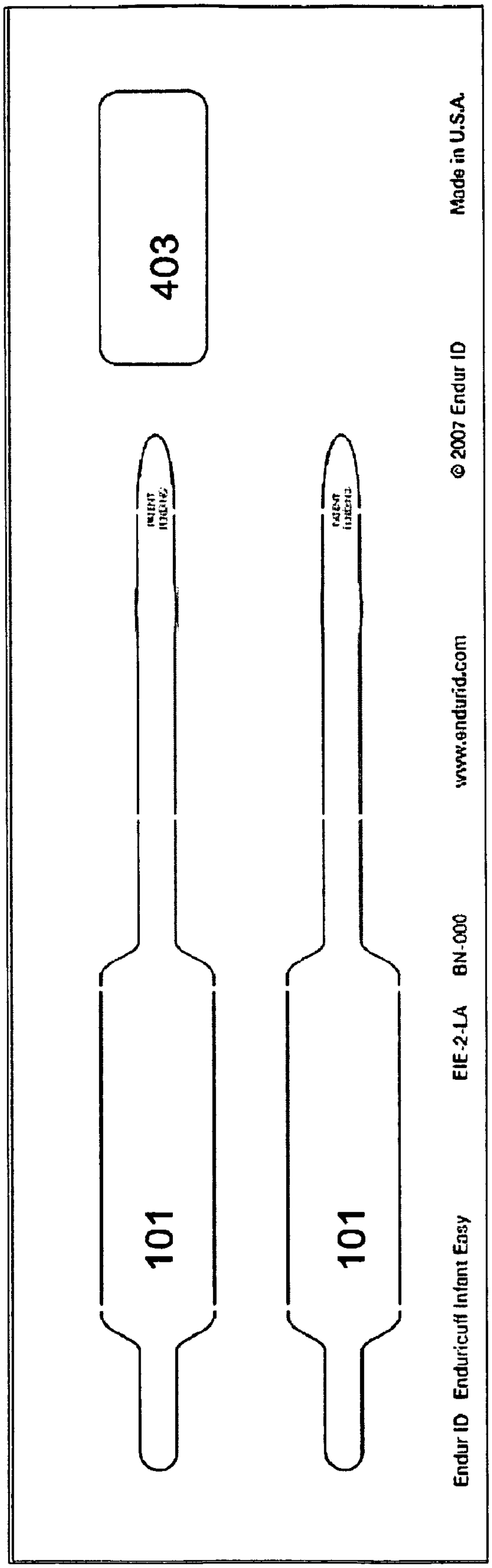
FIG. 4 shows a printable sheet of the presently-preferred embodiment of the wristband.
Figure 5:
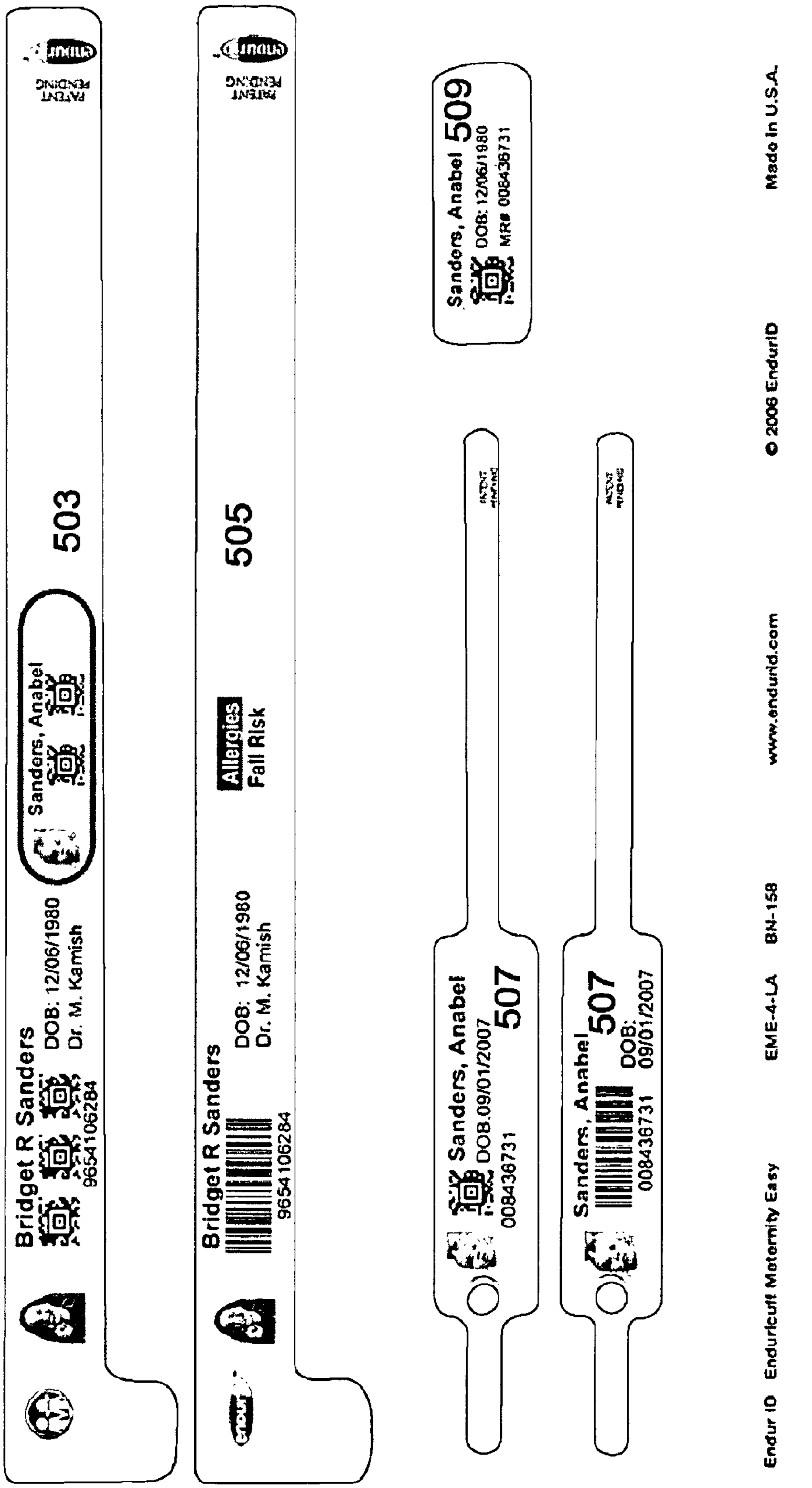
FIG. 5 provides examples of the information that is printed on a wristband.

A Business Form Containing an Array of Bands 101: FIGS. 4 and 5

Bands 101 may be distributed as printable business forms. FIG. 4 shows such a business form 401 that contains two bands 101 and a label 403. The bands and the label 403 will be printed with identification information that relates the label and the band. Business form 401 is made up of two layers: a layer of the material from which the bands are made and a release layer. The bands and the label have been diecut in the layer of material and adhesive has been applied to the bands' adhesive layers. The release layer is coated with a substance that the adhesive does not attach to. The printer on which business form 401 is printed is set up to print identification information on the proper areas of the bands. When the band is used, it is separated from the form along the diecut lines.

FIG. 5 shows the kinds of identification information that is typically placed on the bands. FIG. 5 is a maternity business form that has two adult bands 503 and 505 for the parent(s) of the child, two newborn bands 507 for the child, and a label 509 which can serve to identify the child's crib. All of the wristbands have the name, picture, and barcode for the person identified by the wristband. Band 503 for the mother further includes a picture of the baby and the baby's name and barcode. Other information includes the responsible doctor and medical warnings.

CONCLUSION

The foregoing Detailed Description has disclosed to those skilled in the technologies to which Applicant's techniques pertain how to make and use bands embodying Applicant's techniques and has further disclosed the best mode presently known to the inventor of making and using bands according to his techniques. As will be immediately apparent to those skilled in the relevant technologies, countless other embodiments may be made that employ the techniques disclosed herein. Bands having the hole portion, tongue portion, and adhesive on one or the other or both of the portions can be made of any sheet material. The longer the tongue portion relative to the hole portion, the greater the range of sizes that the loop made from the band may have. Any technique which permits the tongue portion to engage the hole portion may be used to temporarily make the bands into loops. For example, the end of the tongue portion may have an easy release adhesive such as that used on Post-it® notes. If the sheet material has approximately the stiffness of paper, it becomes easier to pass the tongue through the hole. Material of such stiffness also permits hole engagement techniques in which the stiffness of the material causes the edges of the tongue to engage the edges of the hole. The hole may have any shape that is resistant to tearing in the kind of sheet material employed in the bands. The kinds of sheet materials used and other details of other embodiments will depend primarily on the purposes for which the bands are to be used. For all of the foregoing reasons, the Detailed Description is to be regarded as being in all respects exemplary and not restrictive, and the breadth of the invention disclosed herein is to be determined not from the Detailed Description, but rather from the claims as interpreted with the full breadth permitted by the patent laws.

The invention claimed is:

1. Apparatus for forming a band into a persistent loop, the loop having an inner surface and an outer surface and the apparatus comprising:

portions of the band including a hole portion of the band, the hole portion containing a hole and having a first end and a second end;

a tongue portion of the band which is attached to the first end of the hole portion and fits through the hole; and an adhesive attachment area in the hole portion, the adhesive attachment area being located between the hole and the second end of the hole portion and having adhesive on the inner surface of the loop, the band being persistently formed into the loop by passing the tongue portion through the hole from the inner surface and attaching the adhesive to the tongue portion.

2. The apparatus set forth in claim 1 wherein:

the tongue portion has a length which permits the size of the loop to be varied by varying the amount of the tongue portion which is passed through the hole.

3. The apparatus set forth in claim 1 wherein:

the tongue portion includes a structure for mechanically engaging the hole and thereby permitting the band to be temporarily formed into the loop prior to being persistently formed into the loop.

4. The apparatus set forth in claim 3 wherein:

the structure engages an edge of the hole.

5. The apparatus set forth in claim 4 wherein:

the band is made of a material which has substantially the stiffness of writing paper; and the tongue portion passes through the hole without being folded or rotated.

6. The apparatus set forth in claim 4 wherein:

the structure is an edge of the tongue portion.

7. The apparatus set forth in claim 6 wherein:

the structure is an edge of a broadened portion of the tongue portion.

8. The apparatus set forth in claim 1 wherein:

the adhesive attachment area includes a tab.

9. The apparatus set forth in claim 8 wherein:

when the adhesive attachment area is attached to the band, the tab is folded over and attached to the band's inner surface.

10. The apparatus set forth in claim 1 wherein:

the portion of the tongue portion which has passed through the hole is designed to be removed after the adhesive attachment area on the hole portion has been attached to the band.

11. The apparatus set forth in claim 1 further comprising:

a plurality of the adhesive attachment areas, the plurality including the adhesive attachment area in the hole portion and a further adhesive attachment area on the tongue portion

12. The apparatus set forth in claim 1 further comprising:

an information area on the outer surface of the persistent loop.

13. The apparatus set forth in claim 12 wherein:

the information area is on the outer surface of the hole portion of the band.

14. The apparatus set forth in claim 12 wherein:

the information area is on the outer surface of the tongue portion of the band.

15. The apparatus set forth in claim 1 wherein:

the hole has a form which makes the hole resistant to tearing.

16. A business form comprising:

a face ply of sheet material into which a first band suitable for forming an identification bracelet has been die cut, the identification bracelet having an inner surface and an outer surface and the first band including a hole portion of the band which contains a hole and has a first end and a second end, a tongue portion of the band which is attached to the first end of the hole portion and fits through the hole, and an adhesive attachment in the hole portion, the adhesive attachment area being located between the hole and the second end of the hole portion and having adhesive on the inner surface of the bracelet, whereby the band is persistently formed into a loop by passing the tongue through the hole from the inner surface and attaching the adhesive attachment area to the tongue portion; and a liner ply disposed against the face ply, the liner ply comprising:

an outer surface; and an inner surface with a release coating that allows the face ply and liner ply to be separated.

17. The business form set forth in claim 16 wherein:

the first band further has identification information thereon for a wearer of the identification bracelet; and the business form includes another entity which is die cut therein and includes the identification information.

18. The business form set forth in claim 17 wherein:

the other entity is a label.

19. The business form set forth in claim 17 wherein:

the other entity is a second band.

20. The business form set forth in claim 19 wherein:

the second band further has identification information thereon for a wearer of the second band who is associated with the wearer of the first band.

21. A method of forming a band into a persistent loop, the loop having an inner surface and an outer surface and the band having portions including a hole portion of the band which contains a hole and has a first end and a second end, a tongue portion of the band which is attached to the first end of the hole portion and fits through the hole, and an adhesive attachment area, the adhesive attachment area being located between the hole and the second end of the hole portion and having adhesive on the inner surface of the loop, the method comprising the steps of:

passing the tongue portion through the hole from the inner surface; and attaching the adhesive attachment area to the loop's outer surface.

22. The method set forth in claim 21 further comprising the step of:

continuing to draw the tongue portion through the hole until the loop fits closely around an object.

23. The method set forth in claim 21 wherein the method includes the step of:

premaking the loop by passing the tongue portion through the hole, whereby an edge of the tongue engages an edge of the hole to form the premade loop.

24. Apparatus for forming a band into a non-persistent loop prior to making the loop persistent, the loop having an inner surface and an outer surface and the apparatus comprising:

portions of the band including a hole portion of the band which contains a hole and has a first end and a second end;

a tongue portion of the band which is attached to the first end of the hole portion, fits through the hole, and includes a structure for mechanically engaging an edge of the hole; and an adhesive attachment area on a portion of the portions, the band being formed into the non-persistent loop by passing the tongue portion through the hole from the inner surface such that the structure mechanically engages the hole's edge, the mechanical engagement preventing the non-persistent loop from coming apart, whereby the non-persistent loop can be placed over an object, and the non-persistent loop being formed into the persistent loop by attaching the adhesive attachment area to the loop's outer surface.

25. The apparatus set forth in claim 24 wherein:

the band is made of a material which has substantially the stiffness of writing paper; and the tongue portion passes through the hole without being folded or rotated.

26. The apparatus set forth in claim 24 wherein:

the structure is an edge of the tongue portion.

27. The apparatus set forth in claim 26 wherein:

the structure is an edge of a broadened portion of the tongue portion.

28. The apparatus set forth in claim 24 wherein:

prior to attaching the adhesive attachment area, the tongue portion is drawn through the hole until the loop fits closely around the object.

29. The apparatus set forth in claim 24 wherein:

the portion of the tongue portion which has passed through the hole is designed to be removed after the adhesive attachment area has been attached to the band.

30. A method of forming a band into a non-persistent loop prior to making the loop persistent, the loop having an inner surface and an outer surface and the band having portions including a hole portion of the band which contains a hole and has a first end and a second end, a tongue portion of the band which is attached to the first end of the hole portion, fits through the hole, and includes a structure for mechanically engaging an edge of the hole; and an adhesive attachment area on a portion of the portions and, the method comprising the steps of:

forming the nonpersistent loop by passing the tongue portion through the hole such that an edge of the tongue engages an edge of the hole to form the nonpersistent loop; and forming the persistent loop by attaching the adhesive attachment area to the loop's outer surface.

31. The method set forth in claim 30 further comprising the step performed prior to attaching the adhesive attachment area of:

drawing the tongue portion through the hole until the loop fits closely around an object.

32. The method set forth in claim 31 further comprising the step performed after attaching the adhesive attachment area of:

removing the portion of the tongue portion which has passed through the hole.

33. The method set forth in claim 32 further comprising the step performed after attaching the adhesive attachment area of:

removing the portion of the tongue portion which has passed through the hole.

* * * * *

UNITED STATES PATENT AND TRADEMARK OFFICE

CERTIFICATE OF CORRECTION

PATENT NO. : 8,091,261 B2
APPLICATION NO. : 12/519660
DATED : January 10, 2012
INVENTOR(S) : Robert Chadwick It is certified that error appears in the above-identified patent and that said Letters Patent is hereby corrected as shown below:

Column 8, line 31 delete “32” and insert --22--.

Signed and Sealed this
Nineteenth Day of February, 2013

Teresa Stanek Rea
*Acting Director of the United States Patent and Trademark Office*